United States Patent
Vasquez Lipi

(10) Patent No.: US 7,357,923 B1
(45) Date of Patent: Apr. 15, 2008

(54) TOPICAL MEDICAMENT FOR SKIN INJURIES AND DISORDERS

(75) Inventor: Ramon Efrain Vasquez Lipi, Lujan-Mendoza (AR)

(73) Assignee: CAC Pharmaceuticals, McLean, VA (US)

( * ) Notice: Subject to any disclaimer, the term of this patent is extended or adjusted under 35 U.S.C. 154(b) by 0 days.

(21) Appl. No.: 09/810,660

(22) Filed: Mar. 19, 2001

Related U.S. Application Data

(63) Continuation of application No. 09/231,837, filed on Jan. 15, 1999, now abandoned, which is a continuation-in-part of application No. 08/623,970, filed on Mar. 29, 1996, now abandoned.

(60) Provisional application No. 60/008,122, filed on Oct. 30, 1995.

(51) Int. Cl.
*A61K 9/06* (2006.01)

(52) U.S. Cl. .................................. 424/78.06; 514/969

(58) Field of Classification Search ................ 424/401, 424/725, 78.06; 514/871, 937, 944, 969
See application file for complete search history.

(56) References Cited

U.S. PATENT DOCUMENTS

| | | | | |
|---|---|---|---|---|
| 3,431,340 A | * | 3/1969 | George | 424/107 |
| 3,825,563 A | * | 7/1974 | Ahrens | 549/410 |
| 4,386,067 A | * | 5/1983 | Guillon | 424/95 |
| 5,047,232 A | * | 9/1991 | Kaplan | 424/59 |
| 5,503,825 A | * | 4/1996 | Lane | 424/64 |
| 5,597,849 A | * | 1/1997 | McGinity et al. | 514/648 |
| 5,874,479 A | * | 2/1999 | Martin | 514/724 |
| 6,099,866 A | * | 8/2000 | Slimak | 424/520 |

OTHER PUBLICATIONS

Hawley, The Condensed Chemical Dictionary, 10th Ed., Van Nostrand Reinhold Co., New York, (1981), p. 968.*
Soto, L., "Dermal Ointment or Pomade Containing Pure Beeswax and Olive Oil", Derwent Acc. No. 1984-271531 (Oct. 1984), Abstract.*
CAC Pharmaceuticals, Copyright 2001, http://www.jilkon.com/sencil_line.htm, printed on Mar. 13, 2006.*

* cited by examiner

*Primary Examiner*—Sreeni Padmanabhan
*Assistant Examiner*—Gina Yu
(74) *Attorney, Agent, or Firm*—Katten Muchin Rosenman LLP

(57) ABSTRACT

A topical product for the application to the skin or mucosal surfaces comprises yellow beeswax in an oleaginous base of, e.g., olive oil, sunflower oil, almond oil, cod liver oil, castor oil, along with an excipient vehicle. The product is useful in connection with a variety of conditions and ailments of the skin (including burns and abrasions) and mucosal surfaces of, for example, the vaginal and anal areas.

20 Claims, No Drawings

TOPICAL MEDICAMENT FOR SKIN INJURIES AND DISORDERS

CROSS REFERENCE TO RELATED APPLICATIONS

This application is a continuation of application Ser. No. 09/231,837 filed Jan. 15, 1999, now abandoned, which was a continuation-in-part of application Ser. No. 08/623,970 filed Mar. 29, 1996, now abandoned, which claimed the benefit of application Ser. No. 60/008,122, filed Oct. 30, 1995, now abandoned.

FIELD OF THE INVENTION

The present invention relates to an all-natural product for topical application to the skin. In particular, the present invention relates to a product which may be formulated as a topical medicament for treating a wide variety of skin injuries and disorders, or as a topical product for cosmetic use.

BACKGROUND OF THE INVENTION

Burns and other injuries to the skin in which there is capillary obstruction or destruction frequently results in scab formation. Elimination of the scab gives way to a bloody surface where healing accompanied by the formation of granulation tissue occurs. The damaged surface is then re-covered by cells that grow from the periphery towards the center of the injured area, in a process of convergent re-epithelization.

Depending on the location of an injury to the skin, varying degrees of scar retraction can occur. Also, as necrotic tissue, heat, and moisture provide optimal conditions for bacterial growth, when the epidermis is disrupted a bacterial infection can ensue.

Infections caused by bacteria represent the primary factor retarding the normal process of skin re-epithelization. Therefore, in most cases using conventional treatment the timely application of a skin graft is an advisable option for preventing cutaneous sequelae and to ensure healing within an appropriate time frame. Currently available synthetic materials can be used as a palliative measure for graftable injuries.

While today it is increasingly possible to successfully combat pain and bacterial infections associated with injuries to the skin, re-epithelization of the injury is critical factor that must be considered in treating these injuries. In deep burns with destruction of the epidermis and/or the dermis, re-epithelization begins along the edges of the injury and in the other dispersed tegumentary organs. This process is slow and granulation tissue forms in excess prior to the re-covering of the epithelium. Therefore, if not treated as soon as possible with skin grafts, these injuries typically contract, often resulting in the formation of deforming and incapacitating scars.

Improvements in the treatment of burns and other injuries to the skin continue to be sought. A topical medicament which possesses high therapeutic efficacy and which is based upon natural ingredients would be highly desirable.

SUMMARY OF THE INVENTION

The present invention provides a topical medicament for the treatment of a wide variety of injuries to, and disorders of, the skin and various mucosal surfaces. The medicament comprises, as its primary ingredient, an oleaginous base of olive oil, sunflower oil, almond oil, cod liver oil, castor oil and virgin wax. This oleaginous base can be combined with excipients commonly used in the preparation of topically-applied medicaments or cosmetic agents.

Preferred compositions according to the present invention contain from about 10 to about 50 percent by weight of virgin wax (yellow beeswax), based on the total weight of the formulation. Preferred compositions also contain Vitamins A, D and E, which can be provided from natural oleaginous sources or as synthetic additives.

In one embodiment, the invention relates to a topical product for application to the skin comprising about 5% olive oil, about 21% sunflower oil, about 21% almond oil, about 10% cod liver oil, about 3% castor oil and about 23% beeswax, the balance of said product comprising a pharmaceutically-acceptable excipient for topical application to the skin.

Additional features and advantages of the invention will be set forth in the description which follows and will be apparent from the description or may be learned by practice of the invention. For the purposes of this invention, the term "skin" is meant to refer to the epidermis and dermis, as well as mucosal membranes.

DETAILED DESCRIPTION OF THE PREFERRED EMBODIMENTS

Reference will now be made in detail to the presently preferred embodiments of the invention. The present invention provides a topical medicament useful for the treatment of burns and other injuries to and disorders of the skin and mucosal surfaces of the body, including those injuries that result in the loss of epidermal and dermal substance. "Mucosal surfaces" as used herein includes the mucosal surfaces of the vaginal area and anal area, as well as the buccal and nasal mucosal surfaces. The medicament comprises yellow beeswax (also known as "virgin wax") preferably in an oleaginous base that is pharmaceutically acceptable for topical application to the skin and/or mucosal surfaces of the human body. Preferably, the oleaginous base is a mixture of vegetable and animal oils which, when combined in certain proportions, have been found to provide a topical medicament that leads to rapid healing. The topical medicament of the invention has been found to reduce exudate formation and edema and to help clear skin wounds of necrotic tissue and purulent secretions, thus encouraging the appearance of granulation tissue and re-epithelization. The medicament also possesses anti-inflammatory, analgesic, antibacterial, hemostatic and emollient properties. Advantageously, the product does not adhere to wounds.

In a preferred embodiment, the present invention provides a topical product in which the oleaginous base comprises olive oil, sunflower oil, almond oil, cod liver oil and castor oil. Beeswax is combined with this base and an excipient which is pharmaceutically acceptable for topical application to the skin and/or mucosal surfaces of the human body, so as to provide, for example, a cream, gel, lotion or ointment. Preferably, the excipient provides emollient properties.

Olive oil, almond oil, and castor oil are anhydrous vegetable oils made up of liquid or acid, fatty or saturated triglycerides. Olive oil is obtained from the ripe fruit of *Olea europaea* and its crop varieties. Sunflower oil is obtained from the seed/fruit of *Helianthus annus*, and is known to contain about 75 mg Vitamin E (mixed tocopherols) per 100 g. Almond oil is obtained from the seeds of *Prunus amygdalus*.

Cod liver oil is the oil obtained from the fresh livers of *Gadus morrhua* and other species of Gadidae. The oil is extracted from the liver using steam, which breaks down the cellular membranes. Once obtained it is frozen and filtered to separate the stearin. Cod liver oil contains predominantly glycerides with non-saturated fatty acids that together comprise morrhuic acid. It also contains cholesterol, but the most important constituents are vitamins A and D, i.e., retinol and cholecalciferol or vitamin $D_3$. Cod liver oil is known to contain at least about 850 U.S.P. units (255 µg) of Vitamin A per gram, and at least about 85 U.S.P. units (2.125 µg) of Vitamin D per gram.

Castor oil is the cold-drawn oil of the seeds, stripped of the episperm, of *Ricinus communis* and other members of its family Euphorbisceae. It is a slightly yellow to colorless thick, viscous liquid with mild odor or odorless and subtle taste.

As used herein the term "virgin wax" or "yellow beeswax" refers to the product of fusion and purification of the honeycomb of the *Apis mellifera* (*Apidae*) bee after the honey has been separated. Preferably, the topical medicament contains between about 10 and about 50 percent by weight of yellow beeswax, more preferably between about 18 and about 27 percent, and even more preferably between about 23 and about 25 percent. Concentrations greater than about 50 percent by weight generally are not preferred because of the solid consistency of beeswax resulting in an undesirably high viscosity or hardness of the final product. Percentages are expressed throughout this application as percent by weight, based upon the total weight of the product, unless otherwise noted.

Advantageously, the topical medicament contains Vitamins A, D and E. Synthetic versions of these vitamins can be added during formulation, or, preferably, the vitamins can be added via the inclusion of their natural sources, for example, cod liver oil and sunflower oil. The amounts of these vitamins can be varied, as can their sources. Preferred formulations of the medicaments can contain, per 100 g of the final formulation, between about 1275 and about 3825 µg Vitamin A, preferably about 2550 µg; between about 10.625 and about 31.875 µg Vitamin D, preferably about 21.25; and between about 975 and about 3000 mg Vitamin E, preferably about 2025 mg.

The excipients used in the topical medicament of the present invention are comprised primarily of emollients. Emollients are lipids or substances with a similar consistency which, when applied to the skin, protect and soften the skin, making it more supple. Emollients are used primarily as the excipients and bases of ointments and other dermatological preparations. A simple classification of emollients is as follows:

| Emollients for ointments | 1) Oil-based | Hydrocarbons Animal fats | E.g.: Petroleum Jelly |
|---|---|---|---|
| | | Vegetable oils | eg: Castor oil Peanut oil |
| | | Waxes | e.g.: sperm oil |
| | 2) Absorbent bases | Cholesterol Lanolin Cetyl alcohol Stearyl alcohol | |
| | 3) Emulsive bases | Sulfated alcohols Synthetic surface-active agents Acid soaps Basic soaps | e.g.: Stearic acid |
| | 4) Water-soluble bases | e.g. Glycerine | |

1) Oil-based: Oil-based emollients include fats. These products are anhydrous, do not absorb water and are insoluble in it, and are non-washable. Oil-based emollients include: a) hydrocarbons or mineral fats obtained by the distillation of petroleum (petroleum jelly); b) vegetable oils and liquid triglycerides; c) animal fats or solid natural triglycerides.

2) Absorbent bases: These bases are anhydrous and insoluble in water, and are hydrophilic. They typically form water-like emulsions in oil and, thus, can incorporate substances in aqueous solutions. In addition, they are largely non-washable. Absorbent bases include: a) Lanolin or wool fats that are obtained from sheep's wool and made up of fatty acids and cholesterol esters; and b) cetyl and stearyl alcohols, which are solid alcohols obtained by hydrogenation of their respective acids.

3) Emulsive bases: These bases absorb-water, but are insoluble in it, forming water emulsions in oil that are not very washable and can be easily removed from the skin. They include surface active agents (surfactants) which improve wetting of surfaces. They include: a) soaps or salts of fatty acids that may be acidic or basic depending on whether the lipophilic group is anionic or cationic; b) sulfated alcohols which are semi-synthetic substances; and c) synthetic surface active agents.

4) Water soluble bases: These bases are anhydrous, absorb water, and are completely soluble in water. They are also non-fatty and washable. For example, glycerine is obtained from fats and, due to its hydrophobicity, has the property of extracting water from the surface of the mucosa or denuded skin. It does not damage intact skin.

When applied to the skin, these substances, which are in general chemically inert, have a protective and emollient action. The protective action occurs on healthy and diseased skin and prevents the effects of chemical, mechanical, and physical (cold, wind) irritants while decreasing burning and pruritus and producing an anti-inflammatory effect. Since these substances form a more or less impermeable layer over the skin, they prevent drying of the epidermis over the stratum corneum by decreasing the evaporation of water from the cutaneous surface. Thus, the skin is softer and more supple. In this way, emollients mimic the natural sebaceous layer that covers normal skin. The bases envisioned for use in the present invention, including the water soluble ones, are well absorbed by the skin, but almost not at all by the epidermis or the sebaceous glands of the hair follicles.

In practicing the present invention, preferably the excipient is comprised of stearic acid and liquid petroleum jelly, with butylhydroxytoluene (BHT) as a preservative and, optionally, herbal essence. Other excipients can be used in lieu of petroleum jelly, such as olive oil, cod liver oil and other natural oils, depending upon the ultimate consistency that is desired which, in turn, depends upon the ultimate use to which the product will be put. Additionally, other preservatives can be substituted for or used in combination with BHT.

Stearic acid is a mixture of solid fatty acids in variable proportions. It is an absorbent, anhydrous, and non-water soluble base which forms water-type emulsions in oil. When combined with the oil bases, stearic acid increases their consistency (viscosity) and makes them hydrophilic. As used herein, the term herbal essence refers to any of the well-known extracts of aromatic plants, such as an aromatic extract of chamomile.

The topical product of the instant invention, which can be in the form of, for example, a cream or an ointment, can be formulated as products specifically adapted for a variety of applications including skin, vaginal, and proctological creams/ointments. Regardless of the specific formulation and the environment in which the product is utilized, the topical product of the invention shows ability to stimulate granulation and re-epithelization and to act as an anti-pruritic surface analgesic and anti-inflammatory agent.

In treating a subject with a the topical medicament of the present invention, including subjects with venous diseases and ulcerations, the medicament, when in the form of a skin cream or ointment, is preferably spread on a gauze compress to be placed on the effected zone, following which a soft occlusive bandage is applied. When placed over the injury, the compress should extend beyond the injury, for example by about two-thirds of a centimeter. This regimen is repeated about 3 times daily at the beginning of treatment and then less frequently as a favorable course of treatment is observed. The total time of treatment depends upon how rapidly the healing process progresses. In minor household burns, however, as well as in sunburn, the topical medicament of the invention can be applied directly to the affected skin. When treating gynecologic and proctologic conditions, preferably the topical medicament of the invention is administered using a variety of disposable vaginal and proctological applicators as are well known.

In light of the fact that the medicament is applied in a topical fashion, it is not typical to set maximum and minimum doses. Rather, the quantity of the medicament to be applied should be adapted to the extent of the injury. For maximum benefit, the injury should be thoroughly covered by the medicament.

Very little, if any, of the components of medicament are absorbed by the skin or mucosal surface. Thus, no side effects associated with the use of the topical medicament of the invention are expected. In addition, since the contents of the topical medicament are natural substances, the medicament of the invention is well tolerated locally and systemically.

Once prepared, the topical medicament of the invention should be stored in a cool place to maximize its preservation. The final product can be packaged in, for example, 20 g. and 50 g. tubes, or in 50 g., 100 g., 200 g. and 500 g. jars.

The present invention is further described in the following Example, which is provided for illustrative purposes only and is not to be construed as limiting.

Example 1

In order to prepare a 100 g. sample of the topical medicament of the invention, the following ingredients were combined:

| PRIMARY INGREDIENTS | |
|---|---|
| Olive oil | 5.72 g |
| Sunflower oil | 21.72 g |
| Almond oil | 21.72 g |
| Cod liver oil | 10.72 g |
| Castor oil | 3.72 g |
| Virgin wax | 23.40 g |
| EXCIPIENT BASE | |
| Stearic acid | 2.0 g |
| Herbal essence | 0.980 g |
| Butylhydroxytoluene | 0.020 g |
| Liquid petroleum jelly | 10.0 g |

Preparation Step 1

The total quantities of the stearic acid and virgin wax are placed in a stainless steel receptacle outfitted with a double casing. The ingredients are heated to 65° C.-70° C. so that the solids melt.

Preparation Step 2

The melted mass is mixed and the total quantity of castor oil, olive oil, cod liver oil, almond oil, and sunflower oil is added to the mixture.

Preparation Step 3

The total quantity of buthylhydroxytoluene is dissolved in the herbal essence and added to the mixture from step 2.

Preparation Step 4

The total quantity of liquid petroleum jelly (or other medically acceptable excipient) is added and the mixture is mixed for 30 minutes while maintaining the heat and, then, cooling slowly with continuous shaking.

I claim:

1. A composition for application to the skin or mucosal surface to treat burns and other injuries and disorders, consisting of:
   a) from about 18 to about 27 percent by weight of beeswax;
   b) an oleaginous base of about 5% by weight olive oil, about 21% by weight sunflower oil, about 21% by weight almond oil, about 10% by weight cod liver oil, about 3% by weight castor oil;
   c) an added vitamin selected from the group consisting of vitamin A, D and E;
   d) a pharmaceutically acceptable excipient and a preservative.

2. The composition of claim 1, which contains about 23% by weight beeswax, and about 13% by weight of a pharmaceutically-acceptable excipient.

3. The composition of claim 1, which contains between about 23 and about 25 percent by weight of beeswax.

4. The composition of claim 1, which contains Vitamin A.

5. The composition of claim 1, which contains Vitamin D.

6. The composition of claim 1, which contains Vitamin E.

7. The composition of claim 1, which contains Vitamins A, D and E.

8. The composition of claim 1, which contains, per 100 g of the composition, between about 1275 μg and about 3825 μg Vitamin A.

9. The composition of claim 8, which contains about 2550 μg Vitamin A per 100 g of the composition.

10. The composition of claim 1, which contains, per 100 g of the composition, between about 10.625 μg and about 31.875 μg Vitamin D.

11. The composition of claim 10, which contains, per 100 g of the composition, about 21.25 μg Vitamin D.

12. The composition of claim 1, which contains, per 100 g of the composition, between about 975 mg and about 3000 mg Vitamin E.

13. The composition of claim 12, which contains, per 100 g of the composition, about 2025 mg Vitamin E.

14. The composition of claim 1, in which the excipient is liquid petroleum jelly.

15. The composition of claim 1, wherein said preservative is butylhydroxytoluene.

16. A method for treating an injury to the skin or mucosa, which comprises applying to the injured site an effective amount of the composition of claim 1.

17. A method for treating burns and other injuries and disorders of the skin or mucosal surface, which comprises applying to the site in need of treatment an effective amount of a composition consisting of:
   a) from about 18 to about 27 percent by weight of beeswax;
   b) an oleaginous base of about 5% by weight olive oil, about 21% by weight sunflower oil, about 21% by weight almond oil, about 10% by weight cod liver oil, about 3% by weight castor oil;
   c) an added vitamin selected from the group consisting of vitamin A, D and E; and
   d) a pharmaceutically acceptable excipient and a preservative.

18. The method of claim 16, wherein the injury is a burn.

19. The method of claim 17, wherein the injury is a burn.

20. A composition for application to the skin or mucosal surface to treat burns and other injuries and disorders, consisting of:
   a) about 23 percent by weight of beeswax;
   b) an oleaginous base of about 5% by weight olive oil, about 21% by weight sunflower oil, about 21% by weight almond oil, about 10% by weight cod liver oil, about 3% by weight castor oil;
   c) an added vitamin selected from the group consisting of vitamin A, D and E;
   d) a pharmaceutically acceptable excipient and a preservative.

* * * * *